United States Patent
Kuhlmann

(10) Patent No.: US 6,803,456 B1
(45) Date of Patent: Oct. 12, 2004

(54) PROCESS FOR THE PRODUCTION OF ARGININE-SILICATE COMPLEX

(75) Inventor: Erven James Kuhlmann, Hopewell Junction, NY (US)

(73) Assignee: Rutherford Chemicals LLC, Bayonne, NJ (US)

( * ) Notice: Subject to any disclaimer, the term of this patent is extended or adjusted under 35 U.S.C. 154(b) by 0 days.

(21) Appl. No.: 10/639,827

(22) Filed: Aug. 13, 2003

(51) Int. Cl.$^7$ .................. C07H 15/04; C07H 15/00; C07C 229/26
(52) U.S. Cl. ............ 536/18.5; 536/124; 536/121; 562/561; 556/9
(58) Field of Search ................ 536/18.5, 124, 536/121; 562/561; 556/9

(56) References Cited

U.S. PATENT DOCUMENTS 5,707,970 A * 1/1998 McCarty et al. ............ 514/23
6,156,735 A   12/2000 McCarty et al.
6,344,444 B1  2/2002 McCarty et al.

* cited by examiner

Primary Examiner—James O. Wilson
Assistant Examiner—Michael C. Henry
(74) Attorney, Agent, or Firm—Irving M. Fishman

(57) ABSTRACT

A method of making an arginine silicate-containing complex and its use in the prevention and treatment of atherosclerosis and as a dietary supplement are claimed. The arginine silicate complex is synthesized by combining arginine, potassium silicate and inositol.

13 Claims, No Drawings

US 6,803,456 B1

PROCESS FOR THE PRODUCTION OF ARGININE-SILICATE COMPLEX

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates to (1) an improved process for the production of an arginine-silicate-polyol complex and to (2) low copper, low iron, and/or low heavy metals argenine-silicate-polyol complexes.

BACKGROUND OF THE INVENTION

Atherosclerosis is a complex and chronic disease involving the gradual accumulation of lipids, collagen, elastic fibers and proteoglycans in the arterial wall. Current methods of managing atherosclerosis include a low-fat diet, exercise and various cholesterol-lowering drugs. Although these methods can significantly retard the progression of atherosclerosis, they are not entirely satisfactory. U.S. Pat. Nos. 5,707,970; 6,156,735; and 6,344,444 (all of which are incorporated by reference herein in their entirety) teach the utility of arginine-silicate-inositol complexes as well as arginine-silicate-sugar alcohol complexes for the treatment of these conditions. These patents disclose that arginine is combined with inositol or a sugar alcohol and a silicate salt to form a suspension and heated to promote gel formation. The gel is allowed to crystallize and alcohol is added to promote crystallization. The alcohol must ultimately be removed and the removal of the alcohol (which can be up to about 50% of the mass) can be hazardous. In addition, the product that results is an extremely hard material that requires extensive (and expensive) efforts at milling and considerable energy input in order to obtain commercially desirable product. Hence, there is a need to develop improved manufacturing methods that will allow for commercially viable product at a reasonable cost.

OBJECT OF THE INVENTION

It is therefore an object of the invention to provide an improved process for the manufacture of arginine-silicate complexes that avoid the problems of the art.

It is a further object of the invention to provide a method of making arginine-silicate complexes that are commercial batch size viable.

It is yet another object of the invention to provide a process of making arginine-silicate complexes that avoids the use of counter solvents such as ethanol.

Still other objects of the invention will be apparent to those of ordinary skill in the art.

SUMMARY OF THE INVENTION

Surprisingly, it has been found that the above objects can be readily achieved by avoiding the gelling and crystallization steps as set forth in U.S. Pat. Nos. 5,707,970, 6,156,735; and 6,344,444 and spray drying a solution of the arginine-silicate-inositol complex or arginine-silicate-sugar alcohol complex. In one embodiment of the invention, the arginine, silicate salt, and either the inositol or sugar alcohol are combined at elevated temperature to form an initial solution or suspension. The initial solution or suspension is ultimately raised to about at least 80° C. In contrast to U.S. Pat. No. 5,707,970 and its continuation patents, the solution is not permitted to gel and crystallize, nor is a counter solvent added, but rather, while maintaining the complex in solution, the solution is spray dried to result in the desired product.

BRIEF DESCRIPTION OF THE DRAWING

Not Applicable

DETAILED DESCRIPTION OF THE INVENTION

The present invention is an improved process of making an arginine-silicate complexes with either inositol or a sugar alcohol. Arginine is combined with a silicate salt and either inositol or a sugar alcohol at elevated temperature to form a suspension or solution which, if not in solution is heated to result in solution. The initial mixing temperature is preferably at least about 30° C., more preferably at least about 40° C., still more preferably at least about 50° C., even more preferably at least about 60° C. The initial mixing temperature can be chosen to balance energy costs and safety (keeping the temperature as low as possible) and speed of dissolution (raising the temperature as high as practical). Whether or not the initial mixture is a suspension or solution and regardless of the initial mixing temperature, the mixture is to be heated to about at least 80° C., preferably to about at least 90° C., more preferably to about 95° C. to assure proper formation of the desired complex solution prior to the spray drying step. Preferably, once raised to the at least 80° C. temperature, the material (solution/suspension) should be maintained at this temperature for at least about 4 minutes, more preferably for at least about 4.5 minutes, still more preferably at least about 5 minutes. The solution temperature can then be reduced as long as gel formation and crystallization do not take place, and the complex is maintained in solution. Generally, the temperature should not be reduced below about 55° C. in order to maintain the complex in solution before it is spray dried. However, if the solution is allowed to cool below this temperature and the product begins to show some precipitation, heating to above about 55° C. before spray drying will usually bring the precipitate back into solution so that the solution can then be spray dried. In general, the spray drying will take place close to the time of dissolution and raising the temperature to the at least 80° C. temperature, so that little or no appreciable cooling will take place.

Once the arginine-silicate-inositol complex or arginine-silicate-sugar alcohol complex has been formed and is in solution, the solution is introduced into a spray drier. Any spray drying apparatus may be used, but a conical or flat bottom spray drier is preferred.

Since the primary use of the product is for a pharmaceutical or nutritional supplement purpose, pharmaceutically acceptable silicate salts are preferred. Preferably, the silicate salt is potassium silicate, although any other silicate salt that is acceptable for the end use is also suitable. Sodium silicate and magnesium silicate are particularly suitable alternatives, although other suitable silicates will be apparent to those of ordinary skill in this field. Preferably, the silicate has a low iron and/or low copper content so that the final arginine-silicate-polyol complex has a copper content of preferably 0 to not greater than about 50 ppm, more preferably 0 to not greater than about 40 ppm, still more preferably 0 to about 30 ppm, even more preferably 0 to not greater than about 20 ppm, most preferably 0 to not greater than about 10 ppm; and/or an iron content of preferably 0 to not greater than about 100 ppm, more preferably 0 to not greater than about 75 ppm, still more preferably 0 to about 50 ppm, even more preferably 0 to about 40 ppm, most preferably 0 to not greater than about 10 ppm. In addition, preferably the total heavy metal content of the complex should be 0 to not greater than about 20 ppm in order meet the current FDA maximum heavy metal content requirements. Generally commercially available electronic grade silicate material will meet the iron, copper, and heavy metal content requirements above. Furthermore, where the silicate is not a sodium silicate, the sodium content of the final argenine-silicate-polyol complex is preferably 0 to not greater than about 500 ppm, more preferably 0 to not greater than about 400 ppm, even more preferably 0 to not greater than about 350 ppm, most preferably 0 to not greater than about 320 ppm.

The complexes prepared in the present invention method employ a polyol which is generally either inositol or a sugar alcohol. Suitable sugar alcohols include, without limitation, sorbitol, mannitol, xylitol, maltitol, isomalt, lactitol, hydrogenated starch hydrolysates, hydrogenated glucose syrups, erythritol, etc., and mixtures thereof, with sorbitol being a preferred sugar alcohol. Nonetheless, inositol is the most preferred material for the complex so that the most preferred complex for the invention is the arginine-silicate-inositol. For the remainder of this disclosure, reference to the "complex" without qualification means arginine-silicate-inositol complex and/or arginine-silicate-sugar alcohol complex, unless the context dictates otherwise.

In general, the molar ratio of arginine to silicate is about 0.5:1 to about 2:1, preferably about 0.75:1 to about 1.25:1, more preferably about 0.8:1 to about 1.2:1. particularly suitable ratios of arginine:silicate include, among others, 1:1, 0.97:1, and 0.933:1.

The molar ratio of the arginine to polyol (inositol or sugar alcohol) is typically in the range of about 1:1 to about 4:1, preferably about 1.25:1 to about 3:1, more preferably about 1.5:1 to about 3:1. Particularly suitable ratios include, without limitation about 3.25:about 1; about 3:about 1; about 2:about 1; about 1.75:about 1; and about 1.5:about 1.

The mixture resulting from the combination of inositol (and/or sugar alcohol), silicate salt and arginine is a highly viscous suspension/solution which is clarified by heating. In a preferred embodiment, the suspension/solution is heated to between about 80° C. and about 100° C., more preferably about 95° C., until clarification is observed. Generally this requires at least about 4.5 minutes, preferably at least about 5 minutes of maintaining the temperature above the "between about 80° C. and about 100° C." range. At this time, heating and stirring is discontinued. The solution is then introduced into a spray drier to obtain suitable product. Crystallization and gel formation are to be avoided. In those instances where immediate introduction into a spray drier is not possible, the clarified solution should be maintained at a sufficiently high temperature so as to avoid gel formation and crystallization. However, if some crystallization does occur, reheating to at least about 55° C. should redissolve the crystals and the product may then be introduced into the spray drier.

Arginine silicate complexes of the invention method are synthesized as described in the following examples, which are exemplary only and not intended to limit the scope of the invention.

EXAMPLE 1

Prior Art

Arginine (3.8 g, 21.8 mmol) is added to a vigorously stirred solution of inositol (1.25 g, 6.9 mmol) in potassium silicate, {5 ml 29.8°Be, 8.3% $K_2O$ (0.52 g, 5.5 mmol), 20.8% $SiO_2$ (1.3 g, 21.8 mmol)}, resulting in a highly viscous suspension. The suspension is heated to 95° C. Heating and stirring are discontinued when the mixture becomes clear. The mixture is allowed to cool to room temperature and allowed to crystallize. The resulting crystal bulk is dispersed, mixed with ethanol and left for 30 minutes. The crystal bulk is again dispersed and mixed with ethanol and left overnight to complete crystallization. The product is collected by filtration washed with ethanol and dried. The resulting product is extremely hard and not desirable for use in the manufacture of a pharmaceutical or nutritional supplement.

EXAMPLES 2–5

790 g of potassium silicate (Kasil 2529) is added to 684 g of DI water and the mixture is heated to the temperature set forth in the Table below. 205.8 g of inositol is added while holding the temperature constant. While continuing to hold the temperature constant, and with vigorous stirring, 417 g of arginine is added.

| Example # | Initial Temperature |
| --- | --- |
| 2 | 30° C. |
| 3 | 40° C. |
| 4 | 50° C. |
| 5 | 60° C. |

After the dissolution of the bulk of the arginine, the temperature is raised to about 95° C. and held there for 5 minutes. Any arginine that did not dissolve prior to raising the temperature to about 95° C. is now in solution, after which the mixture is introduced into a small R&D conical spray drier utilizing a rotary atomizer with co-current air flow operating at a 177° C. inlet temperature and a 121° C. outlet temperature to give a product having about 46% arginine, about 31% inositol, about 8.6% silicate, and about 5.8% potassium, with molar ratios of about 1.8 arginine::about 2.1 silicate:about 1.2 inositol:1.0 potassium.

EXAMPLE 6

172.7 kg of potassium silicate (Kasil 2529) is added to 171 kg of deionized water and warmed to about 60° C. Then, while holding the temperature at 60° C., 34.3 kg of inositol is added with vigorous stirring. Once these components are in solution and while continuing to hold the temperature at 60° C., 104.25 kg of arginine is added with vigorous stirring. The arginine is completely dissolved at this temperature and the mixture is then raised to about 95° C. and held there for about 5 minutes. The mixture is then spray dried in a 7 foot-diameter by 13 foot-high conical spray drier utilizing a rotary atomizer with co-current air flow operating at a 151° C. inlet temperature and a 86.5° C. outlet temperature. The resulting product has molar ratios of about 3 arginine:about 3 silicate:about 1.0 inositol.

EXAMPLE 7

Samples of the solutions in Examples 2–7 are taken from the solutions that result when the mixtures are held at about 95° C. before spray drying. Those samples are allowed to cool to room temperature. All samples show about the same degree of precipitation. Upon reheating the samples to 50° C., some, but not all of the solids dissolve. However, upon reheating to 55° C., all of the solids dissolve. Samples that completely redissolve are suitable for spray drying into suitable product.

What is claimed is:

1. A process of making a complex of (a) arginine, (b) a silicate, and (c) at least one polyol selected form the group consisting of inositol and sugar alcohols, comprising
    (i) preparing a first solution comprising a pharmaceutically acceptable salt of said silicate, said polyol, and water at an elevated temperature of at least about 30° C.;
    (ii) adding to said first solution said arginine to form a first mixture;
    (iii) heating said first mixture to a temperature of at least 80° C. to form a second solution; and
    (iv) spray drying said second solution
        (A) without allowing said second solution to gel crystallize; or
        (B) after reheating said second solution to at least about 55° C. if said second solution has cooled sufficiently to begin crystallization.

2. The process of claim 1 wherein said first solution is prepared at a temperature of about 40° C.

3. The process of claim 1 wherein said first solution is prepared at a temperature of about 50° C.

4. The process of claim 1 wherein said first mixture is heated to a temperature of about 90° C.

5. The process of claim 1 wherein said first mixture is heated to a temperature of about 95° C.

6. The process of claim 1 wherein said pharmaceutically acceptable salt of said silicate is selected from the group consisting of sodium silicate, potassium silicate, magnesium silicate, and mixtures thereof.

7. The process of claim 1 wherein said second solution is maintained at a temperature of at least 55° C. during said spray drying.

8. The process of claim 1 wherein said first mixture is heated to said at least 80° C. for at least about 4 minutes to form said second solution.

9. The process of claim 1 wherein said pharmaceutically acceptable salt of said silicate is potassium silicate.

10. The process of claim 1 wherein said sugar alcohol is selected from the group consisting of sorbitol, mannitol, xylitol, maltitol, isomalt, lactitol, hydrogenated starch hydrolysates, hydrogenated glucose syrups, erythritol, and mixtures thereof.

11. The process of claim 1 wherein said polyol is inositol.

12. In a process of preparing a complex of arginine, a silicate, and a polyol comprising combining said arginine, said silicate, and said polyol to form a suspension, heating the suspension to form a solution and to promote gel formation, allowing the gel to crystallize, mixing the resulting crystals with an alcohol, and collecting the resulting product, the improvement comprising spray drying said solution while
    (a) avoiding both gel formation and crystallization or
    (b) avoiding gel formation and redissolving any precipitated or crystallized material by reheating to at least 55° C. prior to conducting said spray drying step.

13. The improvement of claim 12 wherein
    (i) a first solution comprising a pharmaceutically acceptable salt of said silicate, said polyol, and water at an elevated temperature of at least about 30° C. is prepared;
    (ii) to said first solution said arginine is added to form a first mixture;
    (iii) said first mixture is heated to a temperature of at least 80° C. to form a second solution; and
    (iv) said second solution is spray dried
        (A) without allowing said second solution to gel or crystallize; or
        (B) after reheating said second solution to at least about 55° C. if said second solution has cooled sufficiently to begin crystallization.

* * * * *